United States Patent [19]

Vurek et al.

[11] Patent Number: 5,119,463
[45] Date of Patent: Jun. 2, 1992

[54] COMPOUND OPTICAL PROBE EMPLOYING SINGLE OPTICAL WAVEGUIDE

[75] Inventors: Gerald G. Vurek, Mountain View, Calif.; Lokanathan M. Iyer, Edmonds; James R. Scott, Bothell, both of Wash.

[73] Assignee: Abbott Laboratories, Abbott Park, Ill.

[21] Appl. No.: 682,555

[22] Filed: Apr. 9, 1991

[51] Int. Cl.⁵ .......................... G02B 5/14; G02B 6/30
[52] U.S. Cl. ...................................... 385/129; 385/12; 128/634
[58] Field of Search .................. 385/129, 130, 12; 264/1.4; 250/227; 128/2, 634, 667; 422/58, 59, 82.07

[56] References Cited

U.S. PATENT DOCUMENTS

| | | | |
|---|---|---|---|
| 2,567,445 | 9/1951 | Parker | 23/250 |
| 3,123,066 | 3/1964 | Brumley | 128/2 |
| 3,612,866 | 10/1971 | Stevens | 250/71 |
| 3,725,658 | 4/1973 | Stanley et al. | 250/71 R |
| 3,754,867 | 8/1973 | Guenther | 232/54 |
| 3,822,695 | 7/1974 | Takayama | 128/2 L |
| 4,075,493 | 2/1978 | Wickersheim | 250/461 |
| 4,200,110 | 4/1980 | Peterson et al. | 128/634 |
| 4,215,275 | 7/1980 | Wickersheim | 250/459 |
| 4,288,159 | 9/1981 | Newman | 356/44 |
| 4,295,470 | 10/1981 | Shaw et al. | 128/634 |
| 4,344,438 | 8/1982 | Schultz | 128/634 |
| 4,437,761 | 3/1984 | Kroger et al. | 356/44 |
| 4,448,547 | 5/1984 | Wickersheim | 374/131 |
| 4,476,870 | 10/1984 | Peterson et al. | 128/634 |
| 4,710,623 | 12/1987 | Lipson et al. | 250/227 |
| 4,712,865 | 12/1987 | Hsu et al. | 350/96.29 |
| 4,727,730 | 3/1988 | Bojarski et al. | 128/667 |
| 4,760,250 | 7/1988 | Loeppert | 250/227 |
| 4,785,814 | 11/1988 | Kane | 128/634 |
| 4,800,886 | 1/1989 | Nestor | 128/634 |
| 4,803,013 | 5/1989 | Maxwell | 128/637 |
| 4,842,783 | 6/1989 | Blaylock | 264/1.4 |
| 4,919,891 | 4/1990 | Yafuso et al. | 422/58 |
| 4,951,669 | 8/1990 | Maxwell et al. | 128/637 |
| 4,954,318 | 9/1990 | Yafuso et al. | 422/59 |
| 5,000,901 | 3/1991 | Iyer et al. | 264/299 |
| 5,006,314 | 4/1991 | Gourley et al. | 422/82.07 |
| 5,019,350 | 5/1991 | Rhum et al. | 422/82.07 |

FOREIGN PATENT DOCUMENTS

| | | |
|---|---|---|
| 0073558 | 6/1982 | European Pat. Off. . |
| 0263693 | 7/1987 | European Pat. Off. . |
| 0336985 | 9/1988 | European Pat. Off. . |

OTHER PUBLICATIONS

Wolfbeis et al., "Recent Progress in Optical Oxygen Sensing," *SPIE*, vol. 906, Optical Fibers in Medicine III, 1988, pp. 42–48.
Gehrich et al., "Optical Fluoresence and its Application to an Intravascular Blood Gas Monitoring System," *IEEE Transactions on Biomedical Engineering*, vol. BME33, No. 2, Feb. 1986, pp. 117–132.
Lubbers et al., "Optical Fluorescence Sensors for Continuous Measurement of Chemical Concentrations in Biological Systems," *Sensors and Actuators*, vol. I, 1983, pp. 641–654.
Vurek et al., "A Fiber Optic PCO2 Sensor," *Annals of Biomedical Engineering*, vol. II, 1983, pp. 499–510.
Peterson et al., "New Technique of Surface Flow Visualization Based on Oxy Quenching of Fluorescence," *Rev. Sci. Instrum.*, vol. 51, No. 5, May 1980, pp. 670–671.
Tusa et al., "Fiber Optic Microsensor for Continuous In-Vivo Measurement of Blood Gases," *SPIE*, vol. 731, Optical Fibers in Medicine II, 1986, pp. 137–143.

*Primary Examiner*—Akm E. Ullah
*Attorney, Agent, or Firm*—Christensen, O'Connor, Johnson & Kindness

[57] ABSTRACT

A $O_2/CO_2/pH$ compound gas probe comprising a single optical waveguide and a method for making the same. The optical waveguide carries light signals at different wavelengths for monitoring oxygen concentration, carbon dioxide concentration, and pH levels. The probe is designed so that light signals used to monitor carbon dioxide concentration are optically prevented from impinging on the sensor used to monitor the pH level.

32 Claims, 3 Drawing Sheets

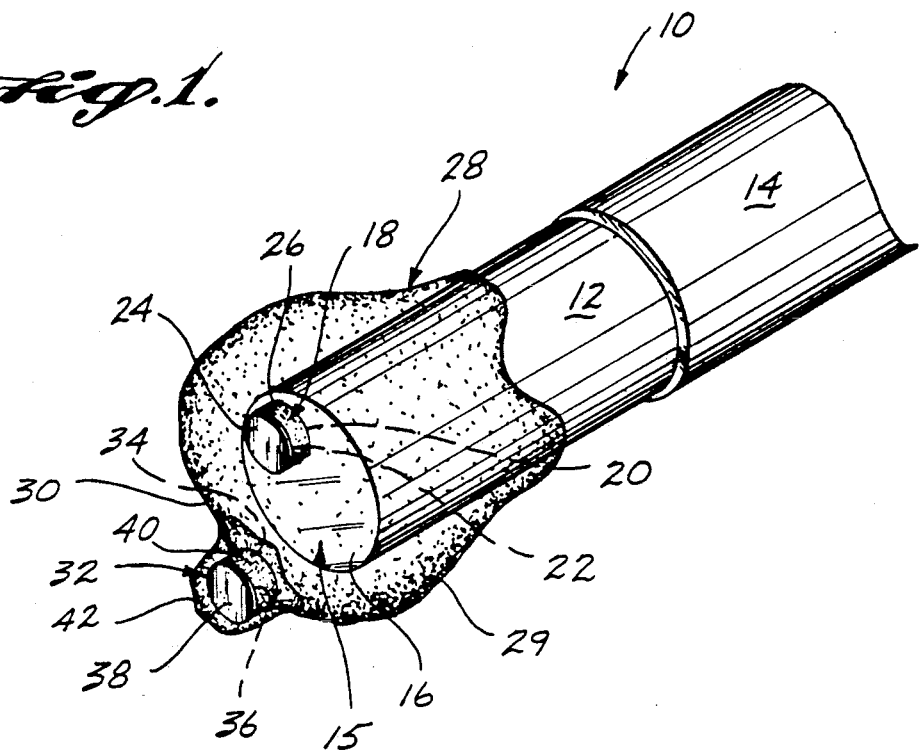
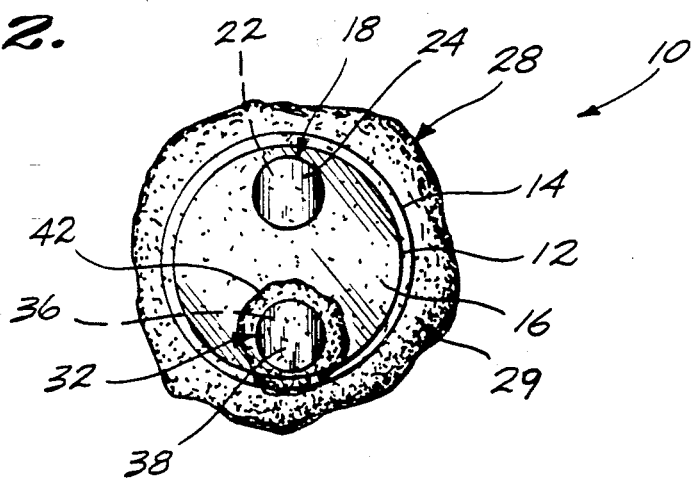
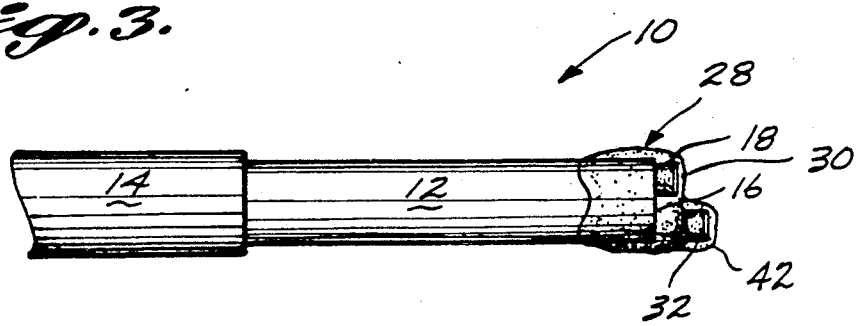

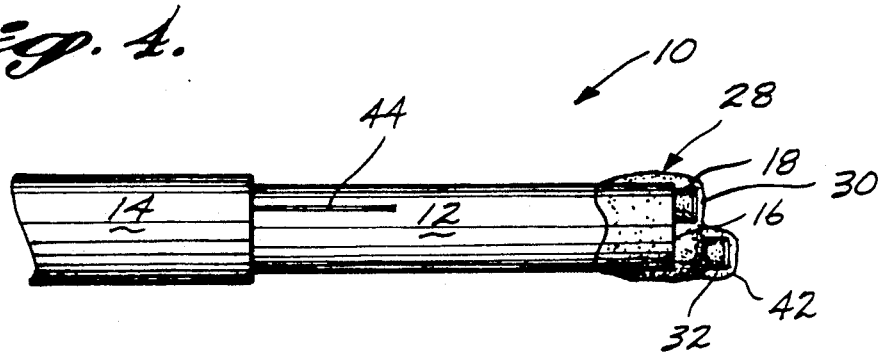

5,119,463

COMPOUND OPTICAL PROBE EMPLOYING SINGLE OPTICAL WAVEGUIDE

TECHNICAL FIELD

This invention relates to fiber-optic compound probes suitable for monitoring chemical analyte concentrations and to a method of making such probes.

BACKGROUND OF THE INVENTION

In recent years, fiber-optic chemical sensors, sometimes called optrodes, have been developed to detect the presence and monitor the concentration of various analytes, including oxygen, carbon dioxide, and hydrogen ions (i.e., pH) in liquids and in gases. Such sensors are based on the recognized phenomenon that the absorbance, and in some cases, the luminescence, that is, the phosphorescence or fluorescence of certain indicator molecules, are specifically perturbed in the presence of specific analyte molecules. The perturbation of the luminescence and/or absorbance profile can be detected by monitoring radiation that is absorbed, reflected, or emitted by the indicator molecule in the presence of a specific analyte.

Fiber-optic sensors relying on these characteristics position the analyte sensitive indicator molecule in a light path at a desired measurement site. Typically, the optical fiber transmits electromagnetic radiation from a light source to the indicator molecule, and the reflectance from or absorption of light by the indicator molecule gives an indication of the gaseous or ionic concentration of the analyte. Alternatively, for monitoring other analytes such as oxygen, the optical fiber transmits electromagnetic radiation to the indicator molecule, exciting it into a type of luminescence, for instance phosphorescence, and the level and/or duration of phosphorescence by the indicator molecule serves as an indication of the concentration of that gas in the surrounding fluid. In the prior art sensors, the indicator molecules are typically disposed in a sealed chamber at the distal end of an optical fiber, and the chamber walls are permeable to the analytes of interest.

One problem with the known sensing systems of the type described is that the optical fiber and chamber attached to the end of the probe are prone to physical damage. The optical fibers with attached sensing chambers are delicate because they are disposed as an external appendage at the end of a probe, extending distally beyond the catheter through which the probe is positioned inside a patient's circulatory system or other physiological features. Any mishandling of the catheter can easily result in damage to the delicate sensor chamber. An additional problem with the known sensing systems described above is that the structure of the chambers and probe configuration often encourage the formation of blood clots or thrombi. Typically, the probes of the prior art comprise discreet optical fibers for each blood gas parameter such as oxygen, carbon dioxide, and pH. This multiplicity of fibers adds to the diameter of the complete probe and provides interfiber crevices that encourage thrombi formation. Furthermore, the complexity and difficulty of manufacturing multifiber probes is well known, due to the small diameters of the fibers and requirements of their arrangement.

Even though a bundled optical fiber probe for sensing a plurality of analytes may have a remarkably small overall cross section, its size can still preclude use in neonatal or pediatric applications in which the patient's veins or arteries are too small in diameter for insertion of the probe assembly. Other problems with known sensing systems relate to the difficulty in reliably placing the sensing end in the environment to be sampled and thereafter continually monitoring the position of the sensor. Correct initial placement of the sensor and maintenance of the initial placement is important in order to obtain reliable results. If the sensor is not correctly placed, the results obtained can be misleading. Correct placement of the sensor is particularly important in the arena of neonatal applications where the presence of analytes such as oxygen, carbon dioxide, and hydrogen ions in a fetus are monitored as a means of evaluating the fetal condition. Prior art multianalyte sensors have failed to effectively deal with several of the problems set forth above.

BRIEF DESCRIPTION OF THE DRAWINGS

The advantages of this invention will become more readily apparent by reference to the following Detailed Description of the Invention, in conjunction with the accompanying drawings wherein:

FIG. 1 is a perspective view of a compound probe for monitoring oxygen, carbon dioxide, and pH levels formed in accordance with the present invention;

FIG. 2 is an end view of the distal end of the probe of FIG. 1;

FIG. 3 is a longitudinal view of the side of the probe shown in FIGS. 1 and 2;

FIG. 4 is a perspective view of an alternative embodiment of a compound probe formed in accordance with the present invention.

SUMMARY OF THE INVENTION

Figure 5:
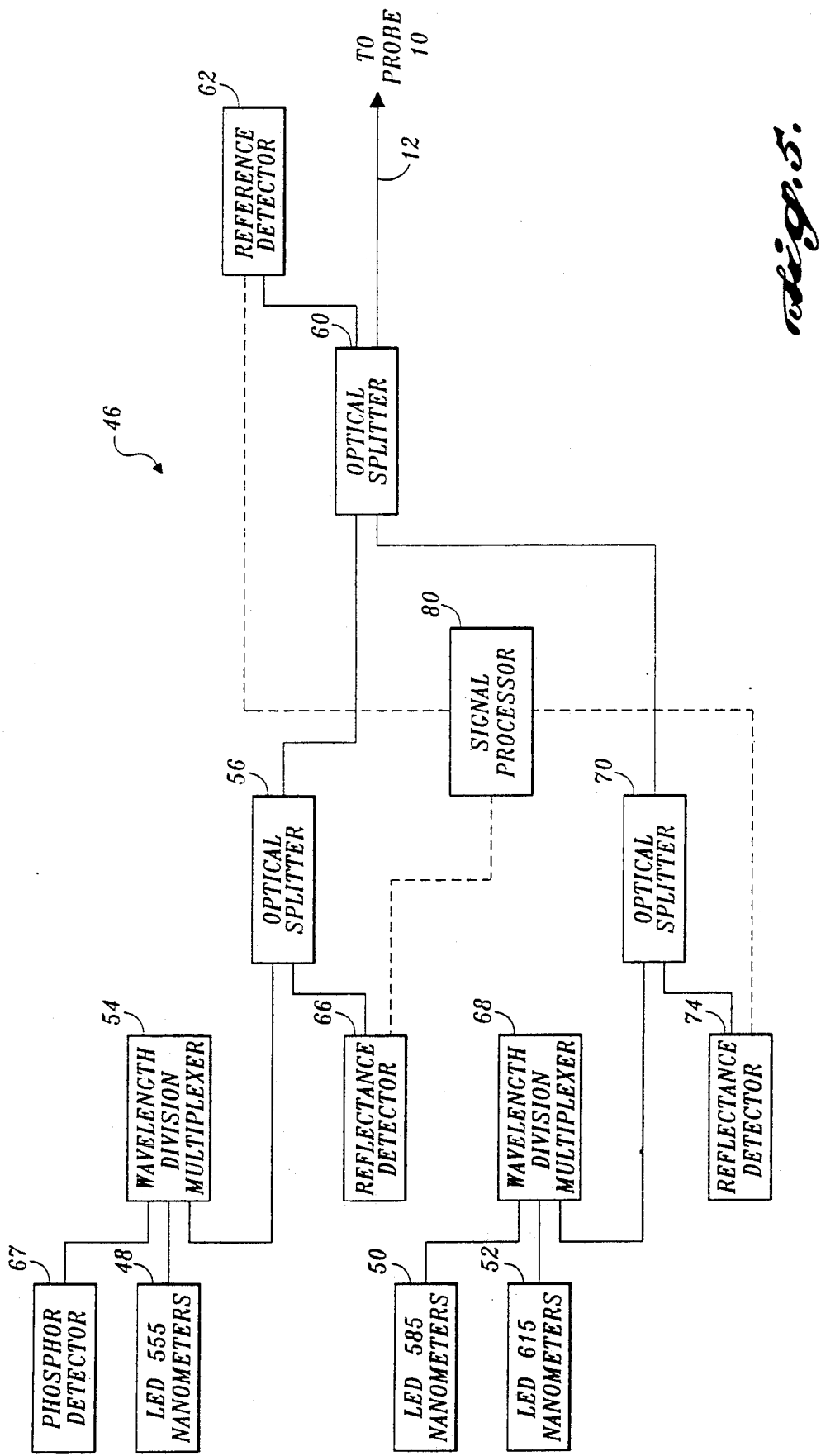
FIG. 5 is a block diagram of an optical system for use with compound probes formed in accordance with the present invention.

The present invention relates to a compound probe that is durable and of a size compatible with neonatal or pediatric applications in patient's veins or arteries. The compound probe can be manufactured without complicated steps. In addition, the probe has a structure that is less susceptible to the formation of thrombi compared to other sensing systems.

In accordance with the present invention, a compound probe for monitoring a plurality of chemical parameters includes an optical waveguide having a longitudinal axis along which light signals at a plurality of wavelengths can be propagated bidirectionally. A first optical sensor is attached to a distal end of the optical waveguide and includes a first analyte indicator. Light signals of a first wavelength are absorbed by the first analyte indicator to an extent dependent upon the concentration of a first analyte present in the environment surrounding the probe. A second optical sensor including a polymer matrix material that includes a second analyte indicator is disposed around the distal end of the optical waveguide and the first optical sensor. Light signals of a second wavelength transmitted to the distal end of the optical waveguide excite the second analyte indicator to emit light. A decay time of the light emission varies in response to a concentration of a second analyte present. A third optical sensor is positioned adjacent to the distal end of the optical waveguide. The third optical sensor includes a third analyte indicator. Light signals of a third wavelength are absorbed by the third analyte indicator to an extent dependent upon the amount of a third analyte present.

In one embodiment of the probe, the first analyte indicator is sensitive to carbon dioxide concentration, the second analyte indicator is sensitive to oxygen concentration, and the third analyte indicator is sensitive to a pH level. The second and third optical sensors can be covered with a coating of the polymer matrix with the third analyte indicator covalently bonded thereto.

Preferably, the first optical sensor comprises a pellet attached to a transverse surface of the optical waveguide at its distal end. In this form of the probe, the pellet covers only a portion of the transverse surface and a polymer matrix material provided with a second analyte indicator encloses the pellet, the transverse surface, and the distal end of the optical waveguide. A second pellet is attached to the surface of the polymer matrix material. This second pellet includes the third analyte indicator.

In another form of the compound probe, the first optical sensor is attached to the distal end of an optical waveguide. The first optical sensor includes a first analyte indicator. Light signals of a first wavelength are absorbed by the first analyte indicator to an extent dependent upon the concentration of a first analyte present. The first optical sensor and the exposed portions of the distal end of the optical waveguide are encased by a polymer matrix including a dye that absorbs light of the first wavelength and transmits light of a second wavelength. A second optical sensor including the second analyte indicator is attached to the polymer matrix. Light signals at the second wavelength are absorbed by the second analyte indicator to an extent dependent upon the amount of a second analyte present. In this form, the polymer matrix and dye may not be sensitive to another analyte; however, they still prevent transmission of light of a first wavelength to the second analyte indicator in the second optical sensor.

A method for making a compound chemical probe comprises a further aspect of this invention. In accordance with the method, a first optical sensor as described above is mounted on at least a portion of a distal end of an optical waveguide. A polymer matrix including a second analyte indicator is applied to the distal end of the optical waveguide, the polymer matrix enclosing the first optical sensor and the portion of the distal end of the optical waveguide that is not occupied by the first optical sensor. A third optical sensor is then mounted onto the polymer matrix to complete the method. Preferably, the polymer matrix including the second analyte indicator and the third optical sensor are coated with another polymer matrix including the third analyte indicator covalently bonded thereto.

DETAILED DESCRIPTION OF THE INVENTION

A preferred embodiment of the compound probe formed in accordance with the present invention is shown in FIGS. 1-3, generally as reference numeral 10. Compound probe 10 includes an optical waveguide 12 which is a single optical fiber encased within a polyimide sheath 14, which covers the entire optical waveguide 12, except for an exposed portion that extends beyond polyimide sheath 14. In this embodiment, the portion of optical waveguide 12 that extends beyond polyimide sheath 14 is preferably about 500 to 700 micrometers in length. It should be understood that optical waveguide 12 can be used in accordance with the present invention without polyimide sheath 14. In fact, in certain applications, it may be preferred not to use polyimide sheath 14. Polyimide sheath 14 adds a strong yet thin protective covering over optical waveguide 12, and is preferred when additional protection is warranted. Optical waveguide 12 has a diameter of approximately 250 micrometers. Larger or smaller diameter waveguides can be used. Optical waveguide 12 can be plastic or glass. The distal end 15 of optical waveguide 12 has a generally planar transverse surface 16, which is cleaved substantially perpendicular to the longitudinal axis of optical waveguide 12.

Bonded to transverse surface 16 is a cylindrical carbon dioxide ($CO_2$) pellet 18, having a first circular surface 20 disposed directly adjacent to transverse surface 16. $CO_2$ pellet 18 is positioned off-center, near the periphery of transverse surface 16.

$CO_2$ pellet 18 includes a second circular surface 22 opposite first circular surface 20. Disposed on second circular surface 22 is a thin film of reflective material 24 (preferably comprising gold foil), which is provided to reflect a light signal propagated through optical waveguide 12. Reflective material 24 is substantially concentric relative to second circular surface 22. It can be appreciated that reflective material 24 and transverse surface 16 of optical waveguide 12 must be substantially perpendicular to the longitudinal axis of optical waveguide 12 to reflect light transmitted through optical waveguide 12 and incident on reflective material 24 back into optical waveguide 12.

$CO_2$ pellet 18 preferably has a longitudinal thickness on the order of 20-30 micrometers and a diameter of about 120 micrometers. $CO_2$ pellet 18 comprises a $CO_2$ analyte indicator molecule such as phenol red codissolved within a polymer matrix (more fully described below), producing a $CO_2$-sensitive indicator material 26 that absorbs light of a predefined wavelength to an extent that depends on the concentration of $CO_2$ around probe 10. $CO_2$-sensitive indicator material 26 also includes a base having a pKa ranging from about 6.0 to 7.8, and preferably 7.0 to 7.5 which ranges overlap the normal physiological range of 7.35 to 7.45. A suitable base includes sodium bicarbonate. $CO_2$ pellet 18 is attached to distal end 15 of optical waveguide 12 using one of the methods described below.

A polymer matrix coating 28 that incorporates an oxygen-quenchable phosphorescent indicator molecule 29, such as porphyrin, surrounds the entire distal end 15 of optical waveguide 12. The relatively high molecular weight porphyrin is insoluble in aqueous solutions and therefore need not be covalently bonded to polymer matrix 28. The specific phosphorescent indicator molecule 29 is preferably selected from among platinum or palladium derivatives or tetrafluorophenylporphyrin, octaethylporphyrin, tetraphenylporphyrin, tetrabenzporphyrin, tetrafluorobenzporphyrin, and tetrachlorobenzporphyrin. Particularly preferred oxygen-quenchable phosphorescent indicator molecules are photostable fluorinated derivatives of such metalloporphyrins. In the physiological oxygen pressure range of 0 to 150 torr, platinum tetraphenylporphyrin provides a lifetime emission curve that is especially suitable for determining oxygen concentration. A preferred method for making coating 28 by mixing the porphyrin into the polymer matrix is described below.

Since $CO_2$ pellet 18 covers a relatively small portion (i.e., less than half of transverse surface 16 of optical waveguide 12, the remaining surface area of transverse surface 16 enables light pulses to readily reach coating 28 and excite the porphyrin contained therein into phosphorescence. Phosphorescent emission by the porphyrin also readily enters the uncovered portion of transverse surface 16 and is propagated back down optical waveguide 12 for determination of its decay time, which provides an indication of the oxygen level around the oxygen sensor.

The distal end 30 of polymer matrix coating 28 is substantially planar and perpendicular to the longitudinal axis of optical waveguide 12. Attached to distal end 30 is a pH pellet 32 having a first circular surface 34 disposed directly adjacent to distal end 30. pH pellet 32 is substantially offset from the center of optical waveguide 12 and is positioned on distal end 30 such that it lies within a light path that does not include $CO_2$ pellet 18.

pH pellet 32 includes a second circular surface 36 opposite first circular surface 34. Disposed on second circular surface 36 is a thin film of reflective material 38 (preferably comprising gold foil), which is provided to reflect a light signal propagated through optical waveguide 12. Reflective material 38 is substantially concentric with second surface 36 of pH pellet 32. It can be appreciated that reflective material 38 and transverse surface 16 must be substantially perpendicular to the longitudinal axis of optical waveguide 12 to reflect light incident on reflective material 38 back into optical waveguide 12.

pH pellet 32 preferably has a longitudinal thickness on the order of 40–60 micrometers and a diameter of about 120 micrometers. pH pellet 32 comprises a pH-sensitive indicator material codissolved within a polymer matrix, producing a pH-sensitive material 40 that absorbs light of a predefined wavelength to an extent that depends on the pH level around pH pellet 32. pH pellet 32 is attached to distal end 30 of oxygen-sensitive polymer matrix coating 28 using one of the methods described below.

Oxygen-sensitive material 29 in the oxygen-sensitive polymer matrix coating 28 absorbs light of a predefined wavelength that cooperates with $CO_2$ pellet 18 to give an indication of the concentration of $CO_2$ around probe 10. By absorbing light of this predefined wavelength, oxygen-sensitive material 29 causes pH pellet 32 to be optically isolated from the light source for the predefined wavelength used in conjunction with $CO_2$ pellet 18.

Light of a predefined wavelength needed to excite the oxygen-sensitive material 29 to phosphoresce is propagated down optical waveguide 12, thus allowing the use of phosphorescent decay times as an indication of the oxygen concentration around the $O_2$ sensor.

In order to measure the pH level around compound probe 10, a predefined wavelength of light is propagated down optical waveguide 12 to distal end 15. This light is transmitted rather than absorbed by oxygen-sensitive material 29 and impinges on pH pellet 32. The predefined wavelength of light is absorbed by pH-sensitive material 40 as a function of the pH level around compound sensor 10. Since the $CO_2$-sensitive material 29 also absorbs some of the predefined wavelength of light used to measure the pH level, the contribution of the $CO_2$-sensitive indicator material must be accounted for as described below.

In an alternative embodiment, oxygen-sensitive material 29 can be replaced by a dye that is not sensitive to oxygen yet has the same light-absorbing properties as the oxygen-sensitive materials described. In other words, the dye absorbs light at the predefined wavelength used to measure carbon dioxide and transmits light that is used to measure the pH level in the surrounding environment of compound probe 10. Although a compound probe formed in accordance with this alternative embodiment provides one less sensor than the compound probe described previously, it may have advantages in those applications where monitoring the oxygen level is of minimal concern.

In still another embodiment, it would be advantageous to use $CO_2$-sensitive indicator molecule and a pH-sensitive molecule that have sensitivities that are totally independent of each other. One way to have sensitivities that are independent is to use indicators whose absorbances do not overlap. This approach would remove the need to account for the contribution from the $CO_2$-sensitive indicator to the pH measurement described above.

A luminescent indicator material could be used for the $CO_2$-sensitive indicator. In this embodiment, the luminescent material preferably emits light of a wavelength that does not overlap the range of wavelengths absorbed by the pH-sensitive indicator or the wavelengths emitted by the $O_2$ sensitive indicator. One example of a suitable luminescent material is fluorscein which emits light at a wavelength of approximately 530 nanometers after being excited by light having a wavelength of about 480 nanometers.

Similarly, the pH sensitive indicator can use a luminescent indicator that emits light at a wavelength that does not overlap the wavelengths absorbed by the $CO_2$ sensitive indicator or the wavelengths emitted by the $O_2$ indicator materials. In addition, the luminescent indicator used in the pH sensor must be excited into luminescence by light having a wavelength that is transmitted through the $O_2$ sensitive indicator material.

Another embodiment of the compound probe 10 formed in accordance with the present invention is illustrated in FIG. 4 and includes the $O_2$, $CO_2$ and pH sensors described above with reference to FIGS. 1–3 with the addition of a thermocouple 44 that is disposed near the probe tip to provide a temperature reading of the environment surrounding compound probe 10. The temperature indication obtained from thermocouple 44 can be used to correct any temperature sensitivities of the other sensors, or for compensation of the measured blood-gas parameters to that which would be read by a blood-gas analyzer at 37° C.

Another use for thermocouple 44 relates to using temperature as a parameter that gives an indication of the placement of the compound probe. The compound probe of the present invention can alternatively be placed subcutaneously in interstitial fluid, in blood vessels, or in certain organs of a patient. Results obtained from the probe can be misleading if the sensitive portion of the probe is not properly placed. For example, when used as a fetal probe to monitor the subcutaneous fluid of the fetal scalp, placement of the tip of the probe within the skin instead of under the skin can result in improper readings. By taking advantage of the known physiological or pathological temperature differences among body structures and between body structures and the environment, confidence checks for proper placement of the probe can be made.

As an example, it is known that the fetal core temperature is about 0.2° C. higher than the maternal core temperature, and the subcutaneous temperature of the fetal scalp may be 1.2° C. higher than the surrounding vaginal maternal temperature. Using the thermocouple near the probe tip makes it possible to determine if the probe is not in the tissue (ambient temperature), within the skin (near ambient temperature), or properly placed beneath the skin (temperature elevation). Using an additional temperature sensor located in the vagina or outside the body, the difference or lack of difference between the temperature sensors would indicate if placement is correct.

Using similar logic, differences in the $O_2$ concentration and $CO_2$ concentration of the fetal scalp, maternal core, and ambient could also be used to determine proper placement of the probe.

The polymer matrix is similar for pH pellet 32 and $CO_2$ pellet 18. The choice of materials for the polymer matrix is influenced by the need to simultaneously satisfy many requirements. For pH pellet 32, the polymer matrix must immobilize the indicator molecule in the light path defined by the axial core of optical waveguide 12. If the indicator molecule is not immobilized, signal drift will result due to leakage of indicator molecules from the polymer matrix, especially leakage of water-soluble molecules such as phenol red. The water-soluble indicator molecules must therefore be covalently bonded to a component of the polymer matrix. In contrast, the preferred phenol red in $CO_2$ pellet 18 need not be covalently bonded to the polymer matrix since coating 28 that encapsulates $CO_2$ pellet 18 is comprised in part of a hydrophobic silicone material. Accordingly, $CO_2$ pellet 18 will not be exposed to aqueous liquids, and therefore the phenol red will not have an opportunity to leak from the polymer matrix.

Further, the polymer matrix must also permit free bidirectional movement of the subject analyte, i.e., the polymer matrix must be permeable to the $CO_2$ and pH analytes. For physiologic applications in which the analyte is dissolved or dispersed in aqueous solutions—for example, as ionic hydrogen—the polymer matrix must be hydrophilic as well as porous to the analyte substance. The hydrophilicity of the polymer matrix must be regulated to prevent undue swelling, and the attendant risk of dissociation from the fiber end. Furthermore, the swelling in an aqueous solution should not cause differential movement of the polymer matrix, vis-à-vis the light-transmitting fiber core, particularly during use of the probe.

The polymer matrix should be capable of sustaining its attachment onto the end of optical waveguide 12 and have a refractive index that is sufficiently matched to that of the optical core to minimize light-scattering effects, such as Fresnel losses. In addition, the polymer matrix should not shrink or crack upon drying. The polymer matrix should also retain its rigidity and strength during use, e.g., by having sufficient wet mechanical strength to maintain its integrity while being manipulated through blood vessels.

One material that satisfies the foregoing requirements is made by copolymerizing a mixture of 94.0 mole percent (mole %), methylmethacrylate (MMA) and about 6.0 mole % methacrylamidopropyltrimethylammonium chloride (MAPTAC) as disclosed in U.S. Pat. No. 4,434,249.

An exemplary protocol for preparing a 94:6 mole/mole % of MMA and MAPTAC is as follows:

1. 1.7 milliliters of 50 weight % aqueous MAPTAC (purified by charcoal chromatography) comprising 0.004 moles MAPTAC obtained, for example, from Polysciences, Warrington, Pa. and 0.05 moles water is mixed with 6.7 milliliters of distilled MMA (0.06 moles), which is also available from Polysciences, 4 milliliters of ethanol, and 20 milligrams of 2,2'-azobisisobutyronitrite.

2. The mixture is allowed to stand in a sealed vial at 75° C. for 24 hours. A 94:6 mole/mole % polymer of MMA/MAPTAC results and can be dissolved in denatured ethanol by stirring 5 grams of the polymer into 50 milliliters of the alcohol overnight. The solution comprises a 10% solution of MMA/MAPTAC polymer.

Polymethylmethacrylate-based materials are an especially appropriate matrix component because they provide a good refractive index match when used with plastic optical fibers having methacrylate cores. This copolymer is highly permeable to water and small ions, especially anions, while meeting all the other attendant requirements mentioned above. Methylmethacrylate can alternatively be copolymerized or alloyed with other ionogenous or neutral monomers, such as hydroxymethylmethacrylate, N-vinylpyrrolidone, or acrylic acid, to confer analyte permeability to the resulting polymer matrix. N-vinylpyrrolidone/aminostyrene copolymer having a weight ratio ranging from 60:40 to 80:20 is another suitable resin material.

Suitable solvents for these resins are known to include alcohols, N,N-dimethylacetamide (DMAC), N,N-dimethylformamide, methylethylketone, tetrahydrofuran, esters, and aromatic and chlorinated hydrocarbons.

The indicator molecule is selected to respond optically to the presence of the targeted analyte (e.g., $CO_2$ or hydrogen ions) when immobilized in the polymer matrix. For continuous monitoring of analyte concentrations, the reaction between the indicator molecule and the analyte should be reversible, as well as sensitive and specific. Suitable analyte-sensitive indicator molecules for other analytes besides $CO_2$ and pH are well known in the art. In addition to phenol red, suitable hydrogen ion indicator molecules include carboxynaphthophthaleim.

As noted earlier for pH pellet 32, covalent bonding functions to immobilize water-soluble indicator molecules within the polymer matrix, but otherwise, must not have a significant adverse impact upon the sensitivity, specificity, and reversibility of the indicator molecule's optical response to the targeted analyte. Thus, analyte-sensitive sites on the indicator molecule must not be eliminated or sterically hindered upon covalent bonding to the polymer. The indicator molecule should therefore be uniformly bound to the polymer in a site-specific manner that preserves the optical responsiveness of the indicator molecule to the analyte. A reaction protocol must therefore be used that prevents or substantially eliminates heterogeneous reaction products.

For this purpose, aminoarylalkylamines are preferably employed to covalently link the indicator molecule to a polymer, which is thereafter admixed in solvent with other matrix components to form an emulsion or solution. Suitable aminoarylalkylamines include those having the formula:

$$NH_2Ar(CH_2)_nH_2$$

wherein Ar is nonsubstituted or preferably substituted phenyl and n is an integer, preferably, n=2, in order to avoid hydrocarbon characteristics associated with longer alkyl chains. The aminoarylalkylamine is preferably para-substituted. Exemplary aminoarylalkylamines for practicing the present invention are 4-(aminophenyl)-ethylamine and 4-(aminophenyl)-propylamine.

Heterogeneous reaction products are prevented by specifically attaching the alkylamino moiety to the polymer before reacting the arylamino moiety with the indicator molecule. The aminoarylalkylamine is first attached to a polymeric resin component, such as the MMA/MAPTAC mixture described above, by reaction in ethanol at 70° C. with triethylamine as a catalyst. The free arylamino group is then reacted with the indicator molecule of choice, for example, by using a diazotization for coupling with indicator molecules such as phenol red that have strong electron releasing groups or by formation of an amidyl linkage with carboxylic acid bearing indicator molecules. The available diazonium binding sites should be saturated with an excess of indicator molecules during the second reaction step in order to provide a polymeric resin component containing a concentrated amount of indicator molecule.

The $CO_2$ indicator molecule need not be covalently bonded to the polymer matrix. In the exemplary formulation of the $CO_2$ pellet without covalent bonding, the following protocol may be followed: about 1.0 weight percent phenol red indicator is admixed or codissolved in a mixture of about 80.0 weight percent MMA/MAPTAC (94.0 mole %/6.0 mole %) copolymer and 20 weight percent polyethylene glycol having a molecular weight of about 600,000. About 5.0 weight percent of the base sodium bicarbonate is also added to the mixture of polymer matrix with indicator. The admixed solution may be sonicated for up to five minutes to ensure homogeneous solution. In an alternative approach, the $CO_2$-sensitive indicator molecule may be covalently bonded with the MMA/MAPTAC polymer using the aminoarylalkylamines noted earlier to form the $CO_2$ polymer matrix solution.

If the probe is to be sterilized using E-beam technology, the $CO_2$ sensor must include an antioxidant compound such as 1,3,5-trimethyl-2,4,6-tris(3,5-di-tert-butyl-4-hydroxybenzyl)benzene (ETANOX TM 330, sold by Ethyl Corporation, Baton Rouge, La.). If the antioxidant is not present when the $CO_2$ sensor is subjected to E-beam sterilization, drastic degradation of the system occurs with apparent loss of the added base. The antioxidant can be admixed in the bicarbonate solution added to the phenol red/MMA/MAPTAC/polyethylene glycol mixture.

Regardless of the particular polymer matrix solution used, chemically bonded or admixed, the next step in the manufacture of the $CO_2$ pellet 18 consists of applying the polymer matrix/$CO_2$ indicator material solution to a reflective material such as gold foil. Suitable gold foil is available from Cominco Electronics Materials of Spokane, Wash. in 1-inch by 12-inch strips that are shipped on a plastic roll. The gold foil is prepared by placing the foil between two clean glass slides and cutting away a 1-centimeter by 2½-centimeter strip. The strip is then cut in half, such that there are two 1-centimeter by 1¼-centimeter pieces. The thickness of each foil piece is measured using conventional devices, e.g., a Mitutoyo Digital Micrometer, and the foil pieces are checked for uniformity before being placed in a scintillation vial to which 1 milliliter of concentrated hydrochloric acid is added. The foil is allowed to soak in the concentrated hydrochloric acid for at least 2 hours, preferably for 8 to 12 hours, to remove any residues on the surfaces of the gold foil. The gold foil is then removed from the vial and rinsed with copious amounts of distilled water, preferably at least three times on each side. After being rinsed, the gold foil is placed on a glass slide and any moisture removed from the surface of the gold foil with blotting paper. Finally, the gold foil is examined for shininess or impurities. If spots/impurities appear evident on the gold foil, it is replaced in the concentrated hydrochloric acid, and the cleaning process repeated.

The gold foil is attached to the glass slide; it is taped down such that the surface of the foil is flat and a 1-centimeter by 1-centimeter of the area of the gold foil is exposed. In this step, it is often advantageous to stretch the gold foil after it is taped down in order to ensure that the surface of the foil is flat. The tape is next masked to prevent the solvents carrying the polymer matrix/indicator material from dissolving the tape mount and, hence, destroying the film preparation. A bead of ultraviolet curable adhesive (e.g., NOA-81 supplied by Norland Products, Inc., New Brunswick, N.J.) is placed along the tape on both sides of the gold foil. Using a No. 2 paint brush, the adhesive is brought over the tape, and up to, but not onto, the surface of the gold foil. Should the NOA-81 adhesive leach onto the gold foil surface, the adhesive is cured under a 365-nanometer ultraviolet lamp, peeled away, and the NOA-81 adhesive applied to the tape again. Once the NOA-81 adhesive has been brought to the edge of the gold foil on both sides such that it completely covers the tape yet does not extend onto the surface of the gold foil, the adhesive is cured by placing it under a 365-nanometer ultraviolet lamp for about 5 minutes.

A leveling plate is placed on top of a Corning hot plate/stirrer, which is set to provide a temperature of about 45°–55° C. The two-way level is used to adjust the height of the screws on the leveling plate until the plate is level. The glass slide carrying the gold foil mount is placed onto the leveling plate and allowed to achieve thermal equilibrium with the plate. The mixture of the MMA/MAPTAC polymer matrix, base, antioxidant, polyethylene glycol, and the $CO_2$ indicator as produced by the process described earlier are placed into an oven and allowed to reach about 45° C. A 50-microliter aliquot of the mixture in N,N-dimethylacetamide (DMAC) (10 wt. % solids/90 wt. % solvent solution) is placed onto the gold foil with a micropipette. Alternatively, ethoxy ethanol can be used as the solvent. The micropipette tip can be used to brush the dye over the entire surface of the gold foil. Care should be taken to ensure that the polymer matrix/$CO_2$ indicator material solution is not applied beyond the edge of the exposed surface of the gold foil. Should this error happen, the sample is removed and the application repeated with a new foil mount. Any bubbles in the film surface should be removed by blowing air through the micropipette tip.

The measured amounts of polymer matrix/$CO_2$ indicator material solution given for the film preparations here are based on an exposed surface for the gold film of one square centimeter. For mounted foils having exposed surface areas other than one square centimeter, the exposed area is multiplied by the amount of solution given for one square centimeter and that amount of solution is applied to the surface of the foil.

Next, a 7-centimeter drying tube is placed over the sample. The leveling plate and the gold foil are left undisturbed allowing approximately 2 hours for the film to dry. After the drying process is complete and the surface inspected for smoothness and impurities, the gold foil is cut from the glass slide and measured for thickness to assure uniformity. Film thickness should not vary by more than 8 micrometers in the area from which the pellets are to be punched.

Using adhesive tape, all four sides of the gold foil should be attached to a flat surface, film side up, allowing the tape to cover about 1 millimeter of the film on each side. Using the end of a bull-nosed tweezers, the adhesive tape is secured to the film by compressing the tape down onto the film surface, being careful not to scrape the film surface. Any excess tape is trimmed so that the film mount is square. The film mount is removed from the flat surface and inverted onto a glass slide. Thin strips of adhesive tape are placed around the underside of the film such that the tape extends over the gold surface but not beyond the tape on the film side of the sample. Again, the end of the bull-nosed tweezers is used to compress the tape securely against the foil. The film mount is centered onto a micropunch XY plate, dye side up, and taped to the XY plate such that the film lies flat and there are no folds in the adhesive tape. The underside of the sample is checked to be sure that the gold foil is clean prior to securing the XY plate to a micropunch (e.g., Model No. 001, Abbott Research, Inc., Bothell, Wash.). The coated gold foil is punched to form a plurality of $CO_2$ pellets 18 that are then used in the construction of the compound probe by attaching the $CO_2$ pellet to the distal end of an optical waveguide as described below.

In a similar manner, pH pellet 32 is constructed. A pH indicator molecule, such as phenol red, is codissolved with the same MMA/MAPTAC polymer matrix that is used in making the $CO_2$ pellets. Because phenol red is water-soluble and the pH pellet 32 is exposed to aqueous fluids during use, it must be covalently bonded to the polymer matrix. Thus, as stated earlier, an aminoarylalkylamine is used to effect the covalent bonding. In one embodiment, 4-(aminophenylethylamine (APE) is attached to the MMA/MAPTAC polymer. Initially, the APE is purified as the dihydrochloride by taking 4 grams of APE (Aldrich Chemical Company, Inc., Milwaukee, Wis.) in 8 milliliters of concentrated hydrochloric acid at 0° C. and recrystallizing the dihydrochloride from a water-ethanol (100 milliliters of 95:5 water-ethanol) mixture. Next, two milliliters of the 10% weight MMA/MAPTAC in denatured ethanol solution described above is azeotroped with anhydrous ethanol using (three 50 milliliter aliquots) and redissolved in 25 milliliters of anhydrous ethanol. 0.38 grams of the APE-dihydrochloride and 1 millimeter of freshly distilled triethylamine (Aldrich) as a catalyst are then added, and the solution stirred in an oven at 55° for 48 hours. The solvent and excess triethylamine are removed in a rotary evaporator.

The MMA/MAPTAC polymer with the APE attached is medium for carrying the phenol red indicator molecule. The coupling of the phenol red to the APE/MMA/MAPTAC matrix is accomplished as follows: The APE/MMA/MAPTAC reaction product is dissolved in 20 milliliters of denatured ethanol at 0° C. To that solution is added 3 milliliters of concentrated hydrochloric acid and 3 milliliters of water. Next, a solution of 0.3 grams of $NaNO_2$ in 2 milliliters of water is added, and the resulting solution stirred at 0° C. for 3 hours. This stirred solution is then added to a solution of 2.4 grams of phenol red (sodium salt of phenol red, Aldrich) and 2.5 grams of potassium bicarbonate in 30 milliliters of water and 30 milliliters of denatured ethanol, while stirring at 0° C. It is important when coupling the diazotized APE polymer to phenol red, that the pH of the solution be maintained at about 8.5 using potassium bicarbonate and that excess phenol red be used to saturate all diazotized sites and prevent diazonium hydroxide/phenol formation. The resulting solution is stirred overnight at 0°.

The solution produced by the preceding coupling reaction is brought to a pH of 1.0 with concentrated hydrochloric acid at 0° C., and 500 milliliters of ice cold water is added. The product is filtered and the residue from the filtration is washed with water (3 aliquots of 100 milliliters). The washed residue is mixed with 2.5 grams of potassium bicarbonate and 250 milliliters water and stirred cell separation is conducted using an F-type membrane (Spectrum Ultra-por, Type F MWCO: 50,000, Spectra Medical Industries, Los Angeles, Calif.) under nitrogen gas. The ultrafiltration is continued until the filtrate is colorless, as indicated by nonabsorption of light having a wavelength of 570 nanometers. The reddish-brown, pure filtered residue product is dried in a dessicator and is referred to as PR/APE/MMA/MAPTAC (PAMM).

Next, sufficient PAMM is added to a 10% solution of MMA/MAPTAC (acid form) in N,N dimethyl-acetamide (DMAC) to produce a solution with 15% PAMM by weight based on solid MMA/MAPTAC. (This solution is referred to as "DEF-1" and may be used to overcoat pH pellet 32 to produce coating 42 as described above.) A 5% solution of polyethylene oxide (PEO) in DMAC is added to part of the DEF-1 solution in sufficient quantity to produce a solution that is from three to five percent PEO solids by weight, producing a solution (referred to as "DEF-1 with PEO") which is used to form pH sensitive indicator material 40.

The preparation of the gold foil for producing pH pellet 32 is identical to that described above in respect to $CO_2$ pellet 18. It can be appreciated that after the application of the adhesive onto the tape surfaces on all four sides of the gold foil, a recess is formed on top of the gold foil such that when the pH sensitive material is applied to the gold foil, the material will stay within the borders of the exposed surface of the gold foil.

Next, 135 microliters of the DEF-1 with PEO solution is applied over the gold foil surface with a digital micropipette. The coated gold foil mount is placed on a level hot plate set to a temperature of from 45° to 55° C. and dried for about 2 hours. The resulting coated gold foil is cut from the glass slide, mounted for punching, and punched immediately. The mounting and punching protocol is identical to that described above for the $CO_2$ pellet. After the pH pellets are thus manufactured, they may be used in the production of the compound probe formed in accordance with the present invention.

The measured amounts of polymer matrix/pH indicator material solution given for the film preparations here are based on an exposed surface for the gold film of one square centimeter. For mounted foils having exposed surface areas other than one square centimeter, the exposed area is multiplied by the amount of solution given for one square centimeter and that amount of solution is applied to the surface of the foil.

An oxygen sensitive polymer matrix, such as used for coating 28 is used for sensing the oxygen analyte. The polymer matrix that carries the $O_2$ sensitive molecule is unlike the polymer matrix used for the $CO_2$ and pH pellets. A hydrophobic 50/50 mole % silicone/polycarbonate material, such as available from Petrach, is used for the $O_2$ polymer matrix. A suitable oxygen analyte indicator molecule is platinum tetrafluorophenylporphyrin (PtTFPP, available from Porphyrin Products, Logan, Utah). Due to its relatively high molecular weight, this porphyrin is insoluble in aqueous solutions and need not be covalently bonded to the polymer matrix by which it is carried.

A typical protocol for the mixture of the PtTFPP indicator molecule into the silicone/polycarbonate polymer matrix is as follows: 0.25 grams of the silicone/polycarbonate and 0.012 grams of the PtTFPP are weighed and mixed together. Next, 2.36 grams of tetrahydrofuran is added to the above constituents. This process results in a 10% solution of oxygen sensitive indicator polymer matrix designated as PT55, which, when solidified, is hydrophobic, but gas-permeable, and is used to form oxygen-sensitive polymer matrix coating 28. The compound probe 10 of the present invention is constructed from $CO_2$ pellet 18, pH pellet 32 and oxygen-sensitive polymer matrix coating 28 described above. The distal end of optical waveguide 12 should be cleaved and polished to produce a square, smooth fiber end. Such a clean, flat fiber end can be prepared by procedures well known in the art for joining optical fibers. The cleaved end of the optical waveguide 12 receives a thin coat of polymethylmethacrylate (not shown). $CO_2$ pellet 18 is then applied after softening the polymethylmethacrylate coating using 2-methoxyethanol. The $CO_2$ pellet should be positioned on the surface of the end of the optical waveguide offset from the axial centerline of the optical waveguide. By so positioning $CO_2$ pellet 18, a substantial portion of the light-guiding cross section of optical waveguide 12 is not blocked by $CO_2$ pellet 18.

After $CO_2$ pellet 18 is attached to the end of optical waveguide 12, the oxygen-sensitive polymer matrix coating 28 is applied to encase $CO_2$ pellet 18 and the portions of the distal end of optical waveguide 12 that are not covered by $CO_2$ pellet 18. Oxygen-sensitive polymer matrix coating 28 is applied by hand-dipping the distal end of optical waveguide 12 into the 10% solution of PT55 until a buildup of between 10 and 200 microns is achieved. The preferred thickness for the oxygen-sensitive polymer matrix coating 28 will depend upon the thickness required to optically isolate pH pellet 32 from the pulse of light used to monitor the carbon dioxide level around compound probe 10. By way of example, thicknesses on the order of 120 microns should be appropriate when a wavelength of approximately 585 nanometers is used to monitor the $CO_2$ level. If the oxygen-sensitive polymer matrix coating 28 is too thin, coating 28 would not prevent the pulses of light from reaching pH pellet 32, which would result in pH pellet 32 providing a contribution to the collected signal for the $CO_2$ measurement. Conversely, if oxygen-sensitive polymer matrix coating 28 is too thick, light transmission is adversely affected, and useful information cannot be collected from the pH pellet 32, which as described below, is positioned on an external surface of oxygen-sensitive polymer matrix coating 28.

While coating 28 is still soft, its distal end is flattened against a smooth, non-stick flat surface. The flattened distal end should be oriented such that it is substantially parallel to the cleaved surface of optical waveguide 12.

pH pellet 32 is applied to the flat surface of coating 28 as described below. If coating 28 has dried, a solvent such as DMAC can be used to soften the coating. After the coating is softened, the pH pellet is applied to the flattened surface. The pH pellet should be positioned on the oxygen-sensitive polymer matrix coating outside the shadow of $CO_2$ pellet 18. In addition, pH pellet 32 should be positioned such that gold foil 38 is substantially parallel to the cleaved end of optical waveguide 12. After the oxygen-sensitive polymer matrix coating 28 and pH pellet 32 are allowed to dry, a coating of DEF-1 is preferably applied by dipping the probe tip therein.

Referring to FIG. 4, when thermocouple 44 is provided, it can be embedded in an epoxy resin provided near the distal end of the compound probe.

The thermocouple is desirable if temperature readings around the probe are desired for the purposes described above.

In order to reduce the opportunity for clot formation, the probe may be coated with an anticoagulant material such as pHEMA, HEMA/N-vinylpyrrolidone copolymer, ethylmethacrylate/polyethylene copolymer and various polyurethanes.

Referring to FIGS. 1 and 5, compound probe 10 further comprises a sensing system 46. Sensing system 46 comprises a trio of light-emitting diodes (LEDs) 48, 50, and 52. LED 48 produces a band of light centered about a wavelength of 555 nanometers; LED 50 produces a band of light centered about a wavelength of 585 nanometers; and LED 52 produces a band of light centered about a wavelength of about 615 nanometers.

Light from LED 48 is used in determining oxygen levels and carbon dioxide levels around compound probe 10. The 555-nanometer wavelength produced by LED 48 is chosen to excite phosphorescence in the PtTFPP carried in the oxygen-sensitive polymer matrix coating 28. The signal from LED 48 travels through a wavelength division multiplexer 54 which filters the signal to remove wavelengths in the red region of the spectrum that would otherwise overlap with the phosphorescence of the PtTFPP. The filter signal is directed to an optical splitter 56. Optical splitter 56 directs the signal to an optical splitter 60, which splits the light so that a portion of the signal is directed to a reference detector 62 and the other portion, to compound probe 10. Reference detector 62 monitors the amplitude of the light pulse produced by LED 48 and in response, produces a reference signal that is used by microprocessor 80 to compensate for variations in the output of LED 48 and system losses. The light pulse from LED 48 that is conveyed to probe 10 causes oxygen-sensitive material 29 in the oxygen-sensitive polymer matrix coating 28 to phosphoresce, emitting light having a wavelength of about 650 nanometers. The time profile of the phosphorescent decay in polymer matrix coating 28 is dependent upon the concentration of oxygen around the probe. The phosphorescent light signal indicative of $O_2$ concentration is collected by optical waveguide 12 and conveyed to optical splitter 60. Optical splitter 60 directs the signal to optical splitter 56, which in turn directs the signal to wavelength division multiplexer 54. Wavelength division multiplexer 54 filters the signal to remove wavelengths in the green region of the spectrum that may be reflected by the carbon dioxide pellet 18 as described in detail below. The signal transmitted to wavelength division multiplexer 54 is sent on to a phosphorescence detector 67. Wavelength division multiplexer is preferred for its filtering capability and its efficient transmission of light. The signal from phosphorescent detector 67 is sent to microprocessor 80 which measures the phosphorescent decay profile. From this phosphorescent decay profile, the oxygen gas concentration is determined. Generally, the higher the concentration of oxygen around the probe, the faster the phosphorescence is quenched.

The pulse of light from LED 48 also serves to provide a measure of $CO_2$ concentration around probe 10. As described above, light having a wavelength of 555 nanometers is transmitted to probe 10. The light passes bidirectionally through $CO_2$ pellet 18 and is reflected by the gold film positioned thereupon. Depending on the extent to which the light pulse is attenuated as a function of the $CO_2$ concentration surrounding the probe, light at the 555-nanometer wavelength is reflected back into optical waveguide 12. This pulse of light does not reach pH pellet 32 because oxygen sensitive polymer matrix coating 28 absorbs the portion of light that does not fall on $CO_2$ pellet 18. The reflected light pulse is directed by optical splitter 60 to optical splitter 56, which in turn directs the reflected signal to a reflectance detector 66. Reflectance detector 66 measures the amplitude of the reflected pulse from LED 48. Microprocessor 80 uses a signal corresponding to this amplitude to determine the degree of absorption of the initial light pulse by the $CO_2$ pellet 18, which is indicative of the level of $CO_2$ around probe 10.

Monitoring of the reflected signal from $CO_2$ pellet 18 and the phosphorescent signal from $O_2$-sensitive polymer matrix coating 28 is separated in time, which allows the use of the same optical circuit. The reflected signal from $CO_2$ pellet is collected during the pulse of light from LED 48; while, the phosphorescent signal is not collected until after the pulse of light from LED 48 is terminated. Due to the dynamics of the optics involved, a residual portion of the reflected signal may exist when the phosphorescent signal is being measured. As discussed above, the filtering provided by wavelength division multiplexer 54 serves to isolate these residual signals.

Shortly after the phosphorescence of oxygen-sensitive material 29 has decayed, LED 50 generates a short pulse of light. This signal is transmitted to a wavelength division multiplexer 68, which directs the signal to an optical splitter 70. Wavelength division multiplexer 68 is preferred for is efficient transmission of light; however an optical splitter can be substituted for wavelength division multiplexer if the loss of transmission efficiency is acceptable. Optical splitter 70 transmits the light signal to an optical splitter 60, which splits the light signal into two parts, directing a portion to reference detector 62 and another portion through optical waveguide 12 to probe 10. Reference detector 62 through microprocessor 80 monitors the amplitude of the light pulse produced by LED 50 and produces a second reference signal that is used to compensate for variations in the output of LED 50 and system losses. The light pulse from LED 50 that is transmitted to probe 10 passes through the oxygen sensitive polymer matrix coating 28 and bidirectionally through pH pellet 32 and is reflected by the gold film positioned thereupon. Depending upon the extent to which the light pulse is attenuated as a function of the pH level surrounding the probe, light at the 585-nanometer wavelength is reflected back through coating 28 into optical waveguide 12. In addition to the reflected signal from pH pellet 32, optical waveguide 12 also collects a reflected signal from $CO_2$ pellet 18. A portion of the light pulse from LED 50 passes bidirectionally through $CO_2$ pellet 18 and is reflected by the gold film positioned thereon. This combined reflected signal is directed by optical splitter 60 to optical splitter 70, which directs the reflected signal to a reflectance detector 74. Reflectance detector 74 measures the amplitude of the reflected pulse from pH pellet 32 and $CO_2$ pellet 18. Microprocessor 80 uses a signal corresponding to this amplitude to determine the degree of absorption of the initial light pulse from LED 50 by pH pellet 32 and measure the level of pH around probe 10.

In order to ascertain the pH level around probe 10 a relationship must be established between the pH level and the signal representing the combined light (from LED 50) that is reflected by $CO_2$ pellet 18 and by pH pellet 32. This relationship is established by removing the portion of the signal that is contributed by light reflected by $CO_2$ pellet 18. Represented mathematically:

$$\text{Signal}_{555} = f_1(CO_2) \tag{1a}$$

$$\text{Signal}_{585} = f_2(CO_2) + g_2(pH) \tag{1b}$$

$\text{Signal}_{555}$ is the reflected portion of the light pulse from LED 48 that is detected by reflectance detector 66.

$\text{Signal}_{585}$ is the reflected portion of the light pulse from LED 50 that is detected by reflectance detector 74.

$f_1(CO_2)$ defines the functional relationship between the $CO_2$ concentration and $\text{Signal}_{555}$.

$f_2(CO_2)$ defines the functional relationship between the $CO_2$ concentration and $\text{Signal}_{585}$.

$g_2(pH)$ defines the functional relationship between the pH level and $\text{Signal}_{585}$.

If $f_1(CO_2) = A + B(CO_2) = \text{Signal}_{555}$, then solving for $(CO_2)$ $$(CO_2) = (\text{Signal}_{555} - A)/B, \tag{1c}$$

where A and B are constants.

If $f_2(CO_2) = C + D(CO_2)$ and $g_2(pH) = E + F(pH)$; then substituting $f_2(CO_2)$ and $g_2(pH)$ into Equation (1b), $$\text{Signal}_{585} = C + D(CO_2) + E + F(pH); \tag{1d}$$

where C, D, E and F are constants.

Then substituting for $(CO_2)$ (from Equation (1c) into Equation (1d), $$\text{Signal}_{585} = C + D[(\text{Signal}_{555} - A)/B] + E + F(pH). \tag{1e}$$

Solving for (pH), $$(pH) = [\text{Signal}_{585} - C - D[(\text{Signal}_{555} - A)/B] - E]/F \tag{1f}$$

The constants A, B, C, D, E and F can be determined empirically to provide a relationship between pH and the collected signals at 555 and 585 nanometers.

After the reflected signals for light from LED 50 are collected and measured, LED 52 produces a pulse of light that includes light having a wavelength of about 615 nanometers. The amplitude of light having this wavelength is unaffected by pH pellet 32, $CO_2$ pellet 18, and oxygen sensitive polymer matrix coating 28. This light pulse is used as a path normalizing signal and is transmitted to wavelength division multiplexer 68, which directs it to optical splitter 70. Optical splitter 70 transmits the light to optical splitter 60, where it is split and a portion is directed to reference detector 62; the balance directed through optical waveguide 12 to compound probe 10. The light pulse from LED 52 is reflected by pH pellet 32 and $CO_2$ pellet 18 and collected by optical waveguide 12. The reflected light pulse is directed by optical splitter 60 to optical splitter 70, which directs the light to reflectance detector 74. Reflectance detector 74 measures the amplitude and produces a corresponding signal that is directed to microprocessor 80 for further processing in accordance with the present invention.

The compound probe formed in accordance with the present invention can be delivered in vivo using a catheter as a delivery device. When positioning the probe, care should be taken to avoid damaging the probe tip. Because of the use of a single optical waveguide as opposed to several waveguides, the probe of the present invention is smaller in scale and will be useful in applications where the size of multiple waveguide probes has been excessive.

Although the present invention has been disclosed in respect to a preferred embodiment and modifications thereto, those of ordinary skill in the art will understand that further changes can be made within the scope of the claims that follow. Accordingly, the scope of the invention should be determined entirely by reference to the claims.

The embodiments of the invention in which an exclusive property or privilege is claimed are defined as follows:

1. A compound probe sensor for monitoring a plurality of chemical parameters, the probe comprising:
   an optical waveguide having a longitudinal axis along which light signals propagate bidirectionally;
   a first optical sensor attached to a distal end of the optical waveguide, said first sensor comprising a first analyte indicator, light signals of a first wavelength being absorbed by the first analyte indicator to an extent dependent upon the amount of a first analyte present;
   a second optical sensor comprising a polymer matrix material in which a second analyte indicator is provided, said polymer matrix material being disposed around the distal end of the optical waveguide and the first optical sensor, light signals of a second wavelength transmitted to the distal end of the optical waveguide exciting the second analyte indicator to emit light, a decay time of the light emission varying in response to a concentration of a second analyte present; and
   a third optical sensor positioned adjacent to the distal end of the optical waveguide, said third optical sensor comprising a third analyte indicator, light signals at a third wavelength being absorbed by the third analyte indicator to an extent dependent upon the amount of a third analyte present.

2. The probe of claim 1, wherein the first analyte indicator is sensitive to carbon dioxide.

3. The probe of claim 2, wherein the first optical sensor comprises phenol red admixed in a polymer matrix.

4. The probe of claim 3, wherein the third optical sensor comprises phenol red covalently bonded to a polymer of methyl methacrylate and methacrylamidopropyltrimethylammonium chloride.

5. The probe of claim 1, wherein the second analyte indicator is sensitive to oxygen.

6. The probe of claim 5, wherein the polymer matrix of the second optical sensor comprises a silicone polycarbonate and the second analyte indicator is a phosphorescent indicator molecule whose phosphorescence is quenched by oxygen.

7. The probe of claim 6, wherein the phosphorescent indicator molecule is a platinum or palladium derivative of tetrafluorophenylporphyrin, octaethylporphyrin, tetraphenylporphyrin, tetrabenzporphyrin, tetrafluorobenzporphyrin and tetrachlorobenzporphyrin.

8. The probe of claim 7, wherein the second analyte indicator absorbs light of the first wavelength.

9. The probe of claim 8, wherein the second analyte indicator transmits light of the third wavelength.

10. The probe of claim 9, wherein the polymer matrix ranges in thickness from 10 microns to 200 microns measured parallel to the longitudinal axis of the optical waveguide.

11. The probe of claim 1, wherein the third analyte indicator is sensitive to a pH level.

12. The probe of claim 1, wherein the first optical sensor comprises a pellet attached to a transverse surface of the optical waveguide at its distal end, the pellet covering less than the entire transverse surface, the second optical sensor comprising a coating of the polymer matrix and the second analyte indicator enclosing the pellet, transverse surface, and the distal end of the optical waveguide.

13. The probe of claim 12, wherein the pellet comprising the first optical sensor further includes a light reflectance material disposed adjacent the first analyte indicator.

14. The probe of claim 12, wherein the third optical sensor comprises a third pellet attached to the coating comprising the polymer matrix and the second analyte indicator.

15. The probe of claim 12, wherein the pellet comprising the third optical sensor further comprises a light reflectance material disposed adjacent said third analyte indicator material.

16. The probe of claim 14, wherein a coating of the third analyte indicator covalently bonded to a polymer matrix encloses the third optical sensor.

17. The probe of claim 1, further comprising a temperature sensor disposed adjacent the distal end of the optical waveguide.

18. The probe of claim 1, wherein the first wavelength and the second wavelength are substantially equivalent.

19. The probe of claim 16, further comprising a first source for the light signals of the first wavelength and the second wavelength, a second source for the light signals of the third wavelength, a first detector for detecting the absorbance of light of the first wavelength by the first analyte indicator, a second detector for detecting the light emission from the second analyte indicator and a third detector for detecting the absorbance of light of the third wavelength by the third analyte indicator.

20. A compound probe for monitoring a plurality of chemical parameters, the probe comprising:
   an optical waveguide having a longitudinal axis along which light signals propagate bidirectionally;
   a first optical sensor attached to a distal end of the optical waveguide, said first sensor comprising a first analyte indicator molecule, said first indicator molecule absorbing light at a first wavelength as a function of the amount of carbon dioxide present;

a second optical sensor comprising a polymer matrix material in which a second indicator molecule is provided, said polymer matrix material being disposed around the distal end of the optical waveguide and the first optical sensor, light signals of a second wavelength transmitted to the distal end of the optical waveguide exciting the second analyte indicator molecule to phosphoresce, a decay time of the phosphorescence varying in response to the amount of oxygen present; and a third optical sensor positioned adjacent to the distal end of the optical waveguide, said third optical sensor comprising a third analyte indicator molecule, said third analyte indicator molecule absorbing light at a third wavelength as a function of a pH level.

21. The probe of claim 20, further comprising a temperature sensor disposed adjacent the distal end of the optical waveguide.

22. A compound probe for monitoring a plurality of chemical parameters, the probe comprising:

an optical waveguide having a longitudinal axis along which light signals propagate bidirectionally;

a first optical sensor attached to a distal end of the optical waveguide, said first optical sensor comprising a first analyte indicator, light signals of a first wavelength being absorbed by the first analyte indicator to an extent dependent upon the amount of a first analyte present;

a second optical sensor positioned adjacent to the distal end of the optical waveguide, said second optical sensor comprising a second analyte indicator, light signals at a second wavelength being absorbed by the second analyte indicator to an extent dependent upon the amount of a second analyte present; and a dye that absorbs light of the first wavelength and transmits light of the second wavelength, the dye being disposed between the first optical sensor and the second optical sensor.

23. The probe of claim 22, wherein the dye is disposed in a polymer matrix, the polymer matrix coating the distal end of the optical waveguide and the first optical sensor.

24. The probe of claim 23, wherein the first analyte indicator is sensitive to carbon dioxide.

25. The probe of claim 24, wherein the second analyte indicator is sensitive to a pH level.

26. The probe of claim 25, further comprising a temperature sensor adjacent the distal end of the optical waveguide.

27. A method of making a compound probe for monitoring a plurality of chemical parameters, the method comprising the steps of:

(a) attaching a first optical sensor on at least a portion of a distal end of an optical waveguide, the optical waveguide having a longitudinal axis along which light signals propagate bidirectionally, the first optical sensor comprising a first analyte indicator, light signals of a first wavelength being absorbed by the first analyte indicator to an extent dependent upon the amount of a first analyte present;

(b) applying a polymer matrix to the distal end of the optical waveguide, the polymer matrix enclosing the first optical sensor and the portion of the distal end of the optical waveguide that is not occupied by the first optical sensor, the polymer matrix including a second analyte indicator, light signals of a second wavelength transmitted to the distal end of the optical waveguide exciting the second analyte indicator to emit light, a decay time of the light emission varying in response to a concentration of a second analyte present; and (c) mounting a third optical sensor on the polymer matrix, the third optical sensor comprising a third analyte indicator, the third optical sensor being positioned on the polymer matrix such that light signals of a third wavelength transmitted to the distal end of the optical waveguide are absorbed by the third analyte indicator to an extent dependent upon the amount of a third analyte present.

28. The method of claim 27, further comprising the step of coating the polymer matrix and third optical sensor with a coating of the third analyte indicator covalently bonded to a second polymer matrix.

29. A system for monitoring a plurality of chemical parameters, the system comprising:

an optical probe including an optical waveguide, light signals of a first wavelength being absorbed by the probe to an extent dependent upon the amount of a first analyte present, light signals of a second wavelength transmitted to the probe causing the probe to emit light, a decay time of the light emission varying in response to a concentration of a second analyte present, light signals at a third wavelength being absorbed by the probe to an extent dependent upon the amount of a third analyte present;

source of light signals of the first wavelength optically coupled to the probe through a first optical pathway, the source also providing light signals of the second wavelength to the probe through the first optical pathway;

means provided in the first optical pathway for detecting the amount of light of the first wavelength absorbed by the probe;

means provided in the first optical pathway for discriminating between the light emission of the probe and the light of the first wavelength;

means provided in the first optical pathway for detecting the light emission of the probe;

source of light signals of the third wavelength optically coupled to the probe through a second optical pathway; and means provided in the second optical pathway for detecting the amount of light of the third wavelength absorbed by the probe.

30. The system of claim 29, wherein the the second optical pathway is optically coupled to a source of a path normalizing signal.

31. The system of claim 29, wherein both the first optical pathway and the second optical pathway include a means for detecting the output from the sources of light signals having the first, second and third wavelengths.

32. The system of claim 29, further comprising a means for processing a signal from the means for detecting the amount of light of the third wavelength absorbed by the probe and converting the signal to a signal that corresponds to an amount of the third analyte present.

* * * * *